US012745742B2

(12) United States Patent
Sevilla García

(10) Patent No.: US 12,745,742 B2
(45) Date of Patent: Sep. 29, 2026

(54) HYBRID TOMATO VARIETY 'E15A51296'

(71) Applicant: Enza Zaden Beheer B.V., Enkhuizen (NL)

(72) Inventor: Francisco Javier Sevilla García, Almeria (ES)

(73) Assignee: Enza Zaden Beheer B.V., Enkhuizen (NL)

( * ) Notice: Subject to any disclaimer, the term of this patent is extended or adjusted under 35 U.S.C. 154(b) by 235 days.

(21) Appl. No.: 18/223,833

(22) Filed: Jul. 19, 2023

(65) Prior Publication Data

US 2024/0023511 A1 Jan. 25, 2024

Related U.S. Application Data

(60) Provisional application No. 63/390,901, filed on Jul. 20, 2022.

(51) Int. Cl.
*A01H 5/10* (2018.01)
*A01H 6/82* (2018.01)

(52) U.S. Cl.
CPC ............... *A01H 6/825* (2018.05); *A01H 5/10* (2013.01)

(58) Field of Classification Search
None
See application file for complete search history.

(56) References Cited

U.S. PATENT DOCUMENTS 11,185,048 B2 * 11/2021 Van Stee .................. A01H 5/08

* cited by examiner

*Primary Examiner* — Jason Deveau Rosen
(74) *Attorney, Agent, or Firm* — Foley Hoag LLP; Brendan T. Jones

(57) ABSTRACT

Hybrid tomato varieties designated 'E15A51293' and 'E15A51296' are disclosed. The disclosure relates to the seeds, plants, and to methods for producing other tomato lines, cultivars, or hybrids derived from the hybrid tomato varieties selected from 'E15A51293' and 'E15A51296'.

19 Claims, 10 Drawing Sheets
(10 of 10 Drawing Sheet(s) Filed in Color)

HYBRID TOMATO VARIETY 'E15A51296'

CROSS-REFERENCE TO RELATED APPLICATIONS

This application claims the benefit of priority to U.S. Provisional Application No. 63/390,901, filed on Jul. 20, 2022, the entire content of which is hereby incorporated by reference.

FIELD

The present disclosure relates to the field of plants and plant breeding. In particular, the present disclosure includes new and distinctive tomato, *Solanum lycopersicum*, hybrid varieties designated 'E15A51293' and 'E15A51296'.

BACKGROUND

Cultivated and commercial forms of tomato belong to the large and diverse genus *Solanum*, which also includes many other flowering plants such as nightshades, potato, and eggplant. It is believed that the tomato species, *Solanum lycopersicum*, originated in the Americas, being native to Ecuador, Peru and the Galapagos Islands, and was initially cultivated by Aztecs and Incas as early as 700 AD. Mexico appears to have been the site of domestication and the source of the earliest introduction. It is thought that the cherry tomato, *S. lycopersicum* var. *cerasiforme*, is the direct ancestor of modern cultivated forms.

As a crop, tomato is grown for its fruit, which is widely used as a fresh market or processed product. The size of tomato fruits may range from small to large, and there are cherry, plum, pear, standard, and beefsteak types. Tomato is grown commercially wherever environmental conditions permit the production of an economically viable yield. For example, in the United States, over 500,000 acres of tomatoes are grown annually, with approximately 40% of tomatoes being grown for fresh market consumption and the rest for processing. The largest market for processing tomatoes in the United States is in California, where processing tomatoes are harvested by machine. California is also the second largest fresh market for tomatoes, the majority of which are harvested by hand at vine ripe and mature green stages of ripeness. Fresh market tomatoes are available in the United States year round. Processing tomato season in California is from late June to September.

*S. lycopersicum* is a simple diploid species with twelve pairs of differentiated chromosomes. The cultivated tomato is self-fertile and almost exclusively self-pollinating. The tomato flowers are hermaphrodites. Commercial cultivars were initially open-pollinated, but most have now been replaced by better yielding hybrids. Due to its wide dissemination and high value, tomato has been intensively bred.

Tomatoes may be grouped by the amount of time it takes for the plants to mature fruit for harvest; in general the cultivars are classified as early, midseason or late-maturing. Tomatoes can also be grouped by the plant's growth habit, which can be determinate or indeterminate. Determinate plants tend to grow their foliage first, then set flowers that mature into fruit if pollination is successful. All of the fruit tend to ripen on a plant at about the same time. Indeterminate tomatoes start out by growing some foliage, then continue to produce foliage and flowers throughout the growing season. These plants tend to have tomato fruit in different stages of maturity at any given time. Recent developments in tomato breeding have led to a wider array of fruit color; in addition to the standard red ripe color, tomatoes can be creamy white, lime green, pink, yellow, golden, or orange.

SUMMARY

Tomato is an important and valuable field crop. Thus, there is a continued need for new tomato varieties. In particular, there is a need for improved tomato varieties that are stable, high yielding, and agronomically sound.

In order to meet these needs, the present disclosure is directed to improved hybrid tomato varieties.

In one aspect, the present disclosure is directed to a hybrid tomato, *Solanum lycopersicum*, seed designated as 'E15A51293', representative sample of seed having been deposited under NCIMB Accession Number X1. In one embodiment, the present disclosure is directed to a *Solanum lycopersicum* tomato plant and parts isolated therefrom produced by growing 'E15A51293' tomato seed (which plants and parts can be referred to, e.g., as 'E15A51293' plants and 'E15A51293' parts, respectively). In another embodiment, the present disclosure is directed to a *Solanum lycopersicum* plant and parts isolated therefrom having all, or essentially all, the physiological and morphological characteristics of a *Solanum lycopersicum* plant produced by growing 'E15A51293' tomato seed having NCIMB Accession Number X1. In still another embodiment of this aspect, the present disclosure is directed to a method of making tomato seeds, the method comprising crossing an 'E15A51293' tomato plant with another tomato plant and harvesting seed therefrom.

Tomato plant parts include tomato leaves, ovules, pollen (pollen grains), seeds, tomato fruits, parts of tomato fruits, flowers, cells, and the like. In one embodiment, the present disclosure is directed to tomato leaves, ovules, pollen, tomato fruits, and/or cells isolated from 'E15A51293' tomato plants. In certain embodiments, the present disclosure is further directed to pollen or ovules isolated from 'E15A51293' tomato plants. In another embodiment, the present disclosure is further directed to protoplasts produced from 'E15A51293' tomato plants. In another embodiment, the present disclosure is further directed to tissue or cell culture of 'E15A51293' tomato plants, and to tomato plants regenerated from the tissue or cell culture, where the plants regenerated from the tissue culture have all, or essentially all, of the morphological and physiological characteristics of 'E15A51293' tomato. In certain embodiments, tissue or cell culture of 'E15A51293' tomato plants is produced from a plant part selected from root, root tip, meristematic cell, stem, hypocotyl, petiole, cotyledon, leaf, flower, anther, pollen, pistil, and/or fruit.

In a further aspect, the present disclosure is directed to a method of producing a seed of an 'E15A51293'-derived tomato plant, including the steps of: (a) crossing a hybrid tomato designated as 'E15A51293', representative sample of seed having been deposited under NCIMB Accession Number X1, with itself or a second tomato plant; and (b) allowing seed of an 'E15A51293'-derived tomato plant to form. In another embodiment of this aspect, the method further includes the steps of: (c) crossing a plant grown from 'E15A51293'-derived tomato seed with itself or a second tomato plant to yield additional 'E15A51293'-derived tomato seed; (d) growing the additional 'E15A51293'-derived tomato seed of step (c) to yield additional 'E15A51293'-derived tomato plants; and (e) repeating steps (c) and (d) for an additional 3-10 generations to generate further 'E15A51293'-derived tomato plants.

In yet another aspect, the present disclosure is directed to a method of vegetatively propagating a plant of hybrid tomato 'E15A51293', the method including the steps of: (a) collecting tissue capable of being propagated from a plant of hybrid tomato 'E15A51293', representative sample of seed having been deposited under NCIMB Accession Number X1; (b) cultivating the tissue to obtain proliferated shoots; and (c) rooting the proliferated shoots to obtain rooted plantlets. In a further embodiment of this aspect, the method further includes step (d) growing plants from the rooted plantlets.

In one aspect, the present disclosure is directed to a hybrid tomato, *Solanum lycopersicum*, seed designated as 'E15A51296', representative sample of seed having been deposited under NCIMB Accession Number 44230. In one embodiment, the present disclosure is directed to a *Solanum lycopersicum* tomato plant and parts isolated therefrom produced by growing 'E15A51296' tomato seed (which plants and parts can be referred to, e.g., as 'E15A51296' plants and 'E15A51296' parts, respectively). In another embodiment, the present disclosure is directed to a *Solanum lycopersicum* plant and parts isolated therefrom having all, or essentially all, the physiological and morphological characteristics of a *Solanum lycopersicum* plant produced by growing 'E15A51296' tomato seed having NCIMB Accession Number 44230. In still another embodiment of this aspect, the present disclosure is directed to a method of making tomato seeds, the method comprising crossing an 'E15A51296' tomato plant with another tomato plant and harvesting seed therefrom.

Tomato plant parts include tomato leaves, ovules, pollen (pollen grains), seeds, tomato fruits, parts of tomato fruits, flowers, cells, and/or the like. In one embodiment, the present disclosure is directed to tomato leaves, ovules, pollen, tomato fruits, and/or cells isolated from 'E15A51296' tomato plants. In certain embodiments, the present disclosure is further directed to pollen or ovules isolated from 'E15A51296' tomato plants. In another embodiment, the present disclosure is further directed to protoplasts produced from 'E15A51296' tomato plants. In another embodiment, the present disclosure is further directed to tissue or cell culture of 'E15A51296' tomato plants, and to tomato plants regenerated from the tissue or cell culture, where the plants regenerated from the tissue or cell culture have all, or essentially all, of the morphological and physiological characteristics of 'E15A51296' tomato. In certain embodiments, tissue or cell culture of 'E15A51296' tomato plants is produced from a plant part selected from root, root tip, meristematic cell, stem, hypocotyl, petiole, cotyledon, leaf, flower, anther, pollen, pistil, and/or fruit.

In a further aspect, the present disclosure is directed to a method of producing a seed of an 'E15A51296'-derived tomato plant, including the steps of: (a) crossing a hybrid tomato designated as 'E15A51296', representative sample of seed having been deposited under NCIMB Accession Number 44230, with itself or a second tomato plant; and (b) allowing seed of an 'E15A51296'-derived tomato plant to form. In another embodiment of this aspect, the method further includes the steps of: (c) crossing a plant grown from 'E15A51296'-derived tomato seed with itself or a second tomato plant to yield additional 'E15A51296'-derived tomato seed; (d) growing the additional 'E15A51296'-derived tomato seed of step (c) to yield additional 'E15A51296'-derived tomato plants; and (e) repeating steps (c) and (d) for an additional 3-10 generations to generate further 'E15A51296'-derived tomato plants.

In yet another aspect, the present disclosure is directed to a method of vegetatively propagating a plant of hybrid tomato 'E15A51296', the method including the steps of: (a) collecting tissue capable of being propagated from a plant of hybrid tomato 'E15A51296', representative sample of seed having been deposited under NCIMB Accession Number 44230; (b) cultivating the tissue to obtain proliferated shoots; and (c) rooting the proliferated shoots to obtain rooted plantlets. In a further embodiment of this aspect, the method further includes step (d) growing plants from the rooted plantlets.

In another embodiment, the present disclosure is further directed to tomato plants, plant parts and seeds produced by the tomato plants where the tomato plants are produced by any of the preceding methods of the disclosure.

In addition to the exemplary aspects and embodiments described above, further aspects and embodiments will become apparent by study of the following descriptions.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 1A shows whole plants and fruit of hybrid tomato 'E15A51293'. FIG. 1B shows the upper sides of typical leaves of hybrid tomato 'E15A51293'. FIG. 1C shows the lower sides of typical leaves of hybrid tomato 'E15A51293'. FIG. 1D shows flowers of hybrid tomato 'E15A51293'. FIG. 1E shows green-mature (right) and full-ripe (left) tomato fruit of hybrid tomato 'E15A51293'. FIG. 1F shows cross-sections (left) and longitudinal sections (right) of full-ripe tomato fruit of hybrid tomato 'E15A51293'. FIG. 1G shows 2-15 cm seedlings of hybrid tomato 'E15A51293' grown under optimal conditions.

FIG. 2A shows whole plants and fruit of hybrid tomato 'E15A51296'. FIG. 2B shows the upper sides of typical leaves of hybrid tomato 'E15A51296'. FIG. 2C shows the lower sides of typical leaves of hybrid tomato 'E15A51296'. FIG. 2D shows flowers of hybrid tomato 'E15A51296'. FIG. 2E shows green-mature fruit (center) of hybrid tomato 'E15A51296'. FIG. 2F shows the full ripe fruit (top) of hybrid tomato 'E15A51296'. FIG. 2G shows cross-sections (left) and longitudinal sections (right) of full-ripe tomato fruit of hybrid tomato 'E15A51296'. FIG. 2H shows 2-15 cm seedlings of hybrid tomato 'E15A51296' grown under optimal conditions.

DETAILED DESCRIPTION

Figure 1B:
FIGS. 1A-1G show hybrid tomato 'E15A51293'.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The selected germplasm is crossed in order to recombine the desired traits and, through selection, varieties or parent lines are developed. The goal is to combine, in a single variety or hybrid, an improved combination of desirable traits from the parental germplasm. These important traits may include, among other things, higher yield, field performance, fruit and agronomic quality such as firmness, color, content in soluble solids, acidity and viscosity, resistance to diseases and insects, and/or tolerance to drought and heat. As tomato fruits may be subject to mechanical harvesting for processing purposes, i.e., juice, paste, catsup, etc., uniformity of plant characteristics such as germination, growth rate, maturity and plant uniformity is also desirable.

Choice of breeding or selection methods can depend on the mode of plant reproduction, the heritability of the trait(s) being improved, and the type of cultivar used commercially (e.g., $F_1$ hybrid cultivar, pureline cultivar). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences the choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from pollinations, and the number of hybrid offspring from each successful cross.

Each breeding program may include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended).

Promising advanced breeding lines are thoroughly tested and compared to appropriate standards in environments representative of the commercial target area(s) for at least three years. The best lines can then be candidates for new commercial cultivars. Those still deficient in a few traits may be used as parents to produce new populations for further selection. These processes, which lead to the final step of marketing and distribution, may take from eight to twelve years from the time the first cross or selection is made.

One goal of tomato breeding is to develop new, unique, and genetically superior tomato inbred lines and hybrids. A breeder can initially select and cross two or more parental lines, followed by repeated selfing and selection, producing many new genetic combinations. A plant breeder can then select which germplasms to advance to the next generation. These germplasms may then be grown under different geographical, climatic, and soil conditions, and further selections can be made during, and at the end of, the growing season. In the case of hybrid variety development, two parental lines may be crossed to produce $F_1$ progeny. A single-cross hybrid is produced when two inbred lines are crossed to produce an $F_1$ hybrid. Once the parental lines that give the best hybrid performance have been identified, the hybrid seed can be reproduced indefinitely as long as the homogeneity of the inbred parent is maintained. Alternatively, a hybrid tomato plant may also serve as a parent in the development of another hybrid tomato plant.

The development of commercial tomato varieties thus requires the development and/or selection of tomato parental lines, the crossing of these lines, and the evaluation of the crosses. Various breeding methods may be used to develop tomato varieties from breeding populations and non-limiting examples of such methods are described herein. Breeding programs can be used to combine desirable traits from two or more varieties or various broad-based sources into breeding pools from which lines are developed by selfing and selection of desired phenotypes. The new lines are crossed with other lines and the hybrids from these crosses are evaluated to determine which have commercial potential. Accordingly, the present disclosure is directed to new hybrid tomatoes 'E15A51293' and 'E15A51296'. Breeding methods involving 'E15A51293' and 'E15A51296' as well as methods of producing and evaluating plants derived from 'E15A51293' and 'E15A51296' are further described herein.

Definitions

In the description and tables that follow, a number of terms are used. In order to provide a clear and consistent understanding of the specification and claims, the following definitions are provided.

Allele: An allele is any of one or more alternative form of a gene, all of which relate to one trait or characteristic. In a diploid cell or organism, the two alleles of a given gene occupy corresponding loci on a pair of homologous chromosomes.

Attachment point: The point on the tomato fruit where the fruit is connected to the tomato plant.

Backcrossing: Backcrossing is a process in which a breeder repeatedly crosses hybrid progeny back to one of the parents, for example, a first generation hybrid $F_1$ with one of the parental genotype of the $F_1$ hybrid.

BRIX: Means a percentage by weight of the sugar in solution (e.g., from a fruit) measured using a refractometer, wherein the fruit is cut in half and the juice within the fruit is squeezed onto a lens. The juice on the lens is then measured by the refractometer.

Determinate tomato: A variety that comes to fruit all at once, then stops bearing. Determinate varieties are best suited for commercial growing since they can be harvested all at once.

Essentially all the physiological and morphological characteristics: A plant having essentially all the physiological and morphological characteristics of another plant means that the plants share essentially all physiological and morphological characteristics identified herein, except, e.g., where applicable, with respect to characteristics derived from a converted gene that differs between the plants as a result backcrossing, mutation, or genetic engineering.

Flesh color: The color of the tomato flesh that can range from orange-red to dark red when at ripe stage (harvest maturity).

Fruit: A ripened ovary, together with any other structures that ripen with the ovary and form a unit.

Grafting: Grafting refers to attaching tissue from one plant to another plant so that the vascular tissues of the two tissues join together.

pH: The pH is a measure of acidity. A pH under 4.35 is desirable to prevent bacterial spoilage of finished products. pH rises as fruit matures.

Plant part: A plant part means any part of a plant including, for example, a cell, protoplast, embryo, pollen grain, ovule, flower, leaf, stem, cotyledon, hypocotyl, meristematic cell, rootstock, root, root tip, pistil, anther, shoot tip, shoot, fruit and petiole.

Predicted paste bostwick: The predicted paste bostwick is the flow distance of tomato paste diluted to 12 degrees brix and heated prior to evaluation. Dilution to 12 degrees brix for bostwick measurement is a standard method used by industry to evaluate product consistency. The lower the number, the thicker the product and therefore more desirable in consistency oriented products such as catsup. The following formula is usually used to evaluate the predicted paste bostwick: Predicted paste bostwick=−11.53±(1.64*juice brix)+(0.5*juice bostwick).

Regeneration: Regeneration refers to the development of a plant from tissue culture.

Relative maturity: Relative maturity is an indication of time until a tomato genotype is ready for harvest. A genotype is ready for harvest when 90% or more of the tomatoes are ripe.

Semi-erect habit: A semi-erect plant has a combination of lateral and upright branching and has an intermediate-type habit between a prostate plant habit, having laterally growing branching with fruits most of the time on the ground, and an erect plant habit, having branching going straight up with fruit being off the ground.

Single gene converted: Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Soluble Solids: Soluble solids refer to the percent of solid material found in the fruit tissue, the vast majority of which is sugars. Soluble solids are directly related to the finished processed product yield of pastes and sauces. Soluble solids are estimated with a refractometer, and measured as degrees brix.

Quantitative Trait Loci (QTL): Quantitative trait loci refer to genetic loci that control to some degree numerically representable traits that are usually continuously distributed.

Uniform ripening: Refers to a tomato that ripens uniformly, i.e., one that has no green discoloration on the shoulders. The uniform ripening is controlled by a single recessive gene.

Vegetative propagation: Refers to taking part of a plant and allowing that plant part to form roots where plant part is defined as leaf, pollen, embryo, cotyledon, hypocotyl, meristematic cell, root, root tip, pistil, anther, flower, shoot tip, shoot, stem, fruit and petiole.

Viscosity: The viscosity or consistency of tomato products is affected by the degree of concentration of the tomato, the amount and extent of degradation of pectin, the size, shape and quality of the pulp, and probably to a lesser extent, by the proteins, sugars and other soluble constituents. The viscosity is measured in Bostwick centimeters by using instruments such as a Bostwick Consistometer.

Overview of Hybrid Tomato 'E15A51293'

Figure 1A:
Figure 1C:
Figure 1D:
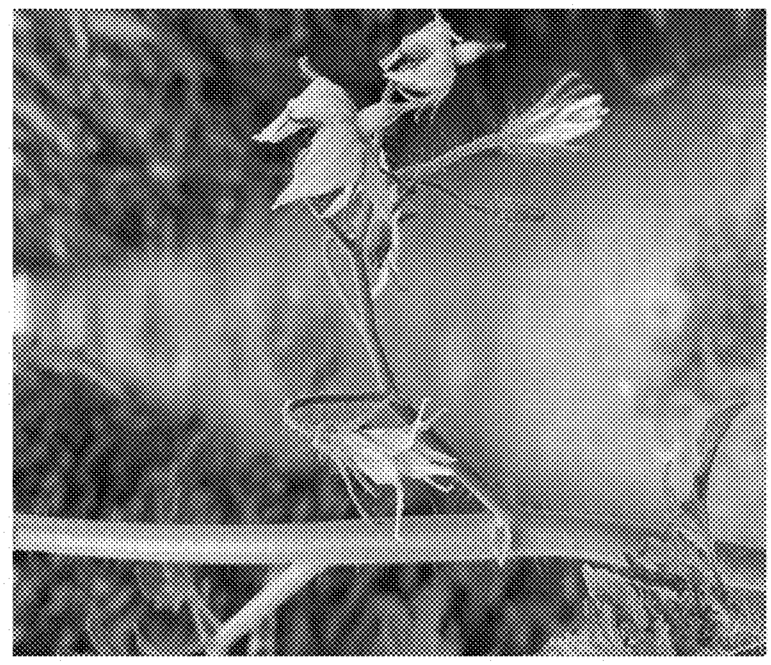
Figure 1F:
Figure 1E:
Figure 1G:

Hybrid tomato 'E15A51293' has medium leaf cover and produces 6 to 7 fruits per cluster and up to 15 clusters total. 'E15A51293' is suitable for fresh market use. Further, hybrid tomato 'E15A51293' is adapted to greenhouse growing methods, in particular, to a hydroponic growing system. In addition, hybrid tomato 'E15A51293' is highly resistant to the pathogen Tomato Brown Rugose Fruit Virus (ToBRFV), resistant to the pathogens Tobacco Mosaic Virus (ToMV) races 0, 1, and 2, Tomato spotted wilt virus (TSWV), *Fusarium oxysporum* f. sp. *lycopersici* (Fol) races 0, 1, and 2, and *Verticillium* wilt (*Verticillium albo-atrum* (Va) (race 0), *Verticillium* dahlia (Vd) (race 0)); moderately resistant to the pests Root-knot nematode (*Meloidogyne arenaria* (Ma), *Meloidogyne incognita* (Mi), *Meloidogyne javanica* (Mj)); highly resistant to the fruit disorder bursting, zippering and silvering; resistant to fruit disorders catface and fruit pox; and moderately resistant to the fruit disorders greywall, gold fleck, blossom end rot, radial cracking; and concentric cracking; In addition, hybrid tomato 'E15A51293' moderately resistant to the pests root-knot nematode (*Meloidogyne arenaria* (Ma), *Meloidogyne incognita* (Mi), *Meloidogyne javanica* (Mj)) FIG. 1A shows whole plants and fruit of hybrid tomato 'E15A51293'. FIG. 1B shows the upper sides of typical leaves of hybrid tomato 'E15A51293'. FIG. 1C shows the lower sides of typical leaves of hybrid tomato 'E15A51293'. FIG. 1D shows flowers of hybrid tomato 'E15A51293'. FIG. 1E shows green-mature (right) and full-ripe (left) tomato fruit of hybrid tomato 'E15A51293'. FIG. 1F shows cross-sections (left) and longitudinal sections (right) of full-ripe tomato fruit of hybrid tomato 'E15A51293'. FIG. 1G shows 2-15 cm seedlings of hybrid tomato 'E15A51293' grown under optimal conditions. Hybrid tomato 'E15A51293' is the result of numerous generations of plant selections from its parent lines, and was chosen for its plant size, medium vigor and leaf cover, good fruit setting, amount of fruit per cluster and number of fruit clusters produced, fruit weight, fruit shape and uniformity, and its resistances to Tobacco mosaic virus (ToMV) (highly resistant), Tomato Brown Rugose Fruit Virus (ToBRFV) (resistant), Tomato spotted wilt virus (TSWV) (resistant), *Verticillium* wilt, *Fusarium oxysporum* f. sp. *lycopersici* (Fol) (resistant), and root-knot nematode (moderately resistant). The resistances to ToBRFV and Fol were of particular importance for selection.

Hybrid tomato 'E15A51293' has shown uniformity and stability for the traits, within the limits of environmental influence for the traits. The hybrid has been increased with continued observation for uniformity. No variant traits have been observed or are expected in hybrid tomato 'E15A51293'.

Objective Description of the Hybrid Tomato 'E15A51293'

In various embodiments, 'E15A51293' can be characterized by the following morphologic and other characteristics as outlined in Table 1. The data which define these characteristics is based on observations taken in Culiacan, Mexico. Measurements of 'E15A51293' plants were made twenty weeks after seeding.

TABLE 1

Morphologic and other characteristics of 'E15A51293'.
Variety Description Information For 'E15A51293'

| SEEDLING: | |
|---|---|
| Anthocyanin in hypocotyl of 2-15 cm seedling: | Absent |
| Habit of 3-4 week old seedling: | Compact |

TABLE 1-continued

| Morphologic and other characteristics of 'E15A51293'. Variety Description Information For 'E15A51293' | |
|---|---|
| MATURE PLANT: | |
| Plant height (in cm): | 500 to 600 |
| Growth type: | Indeterminate |
| Form: | Compact |
| Size of canopy: | Medium |
| Diameter (in cm): | 30 to 40 |
| Height (in cm): | 5 to 8 |
| Habit: | Erect |
| GROWTH CONDITION: | |
| Type of culture: | Greenhouse |
| Main use: | Fresh market |
| Mechanical harvest: | Not suitable |
| Suitable growing region: | Mexico, Spain |
| Growing system: | Hydroponic |
| Planting period: | Late August to late November |
| Harvesting period: | November to June |
| STEM: | |
| Branching: | Intermediate |
| Branching at cotyledonary or first node: | Absent |
| Number of nodes between first inflorescence: | 1 to 4 |
| Number of nodes between early (first to second, second to third) inflorescences: | 2 to 3 |
| Number of nodes between later developing inflorescences: | 2 to 3 |
| Pubescence on younger stems: | Moderately hairy |
| LEAF: | |
| Type of blade: | Tomato |
| Morphology: | Type 2 |
| Margin of major leaflets: | Nearly entire |
| Margin rolling or wiltiness: | Moderate |
| Onset of leaf rolling | Late season |
| Surface of major leaflets: | Smooth |
| Pubescence: | Normal |
| INFLORESCENCE: | |
| Type: | Simple |
| Average number of flowers in inflorescence: | 6 to 7 |
| Leafy or "running" inflorescences | Absent |
| FLOWER: | |
| Calyx shape: | Normal, lobes awl-shaped |
| Calyx lobe length: | Approximately equaling corolla |
| Corolla color: | Yellow |
| Style pubescence: | Absent |
| Anthers: | Separating into two or more groups at anthesis |
| Fasciation (first flower of third inflorescence): | Absent |
| FRUIT: | |
| Typical fruit shape: | Obovate |
| Shape of transverse section: | Round |
| Shape of stem end: | Flat |
| Shape of blossom end | Tapered |
| Shape of pistil scar: | Stellate |
| Ribbing at peduncle end: | Absent or very weak |
| Abscission layer: | Present (pedicellate) |
| Point of detachment of fruit at harvest: | At pedicel joint |
| Pedicel length (from joint to calyx attachment, in mm): | 10 |
| Length of mature fruit (stem axis, in mm): | 120 |
| Diameter of fruit at widest point (in mm): | 60 |
| Average weight of mature fruit (in grams): | 155 to 165 |
| Number of locules: | 2 to 4 |
| Fruit surface: | Smooth |
| Green shoulder (before maturity): | Absent |
| Full ripe fruit color: | Red |
| Full ripe fruit flesh color: | Red/Crimson |
| Uniformity of flesh color: | Uniform |
| Stem scar size: | Small |
| Core: | Present |
| Thickness of pericarp (in mm): | 5 |
| Firmness: | Firm |
| Fruit shelf-life: | Medium |

TABLE 1-continued

| Morphologic and other characteristics of 'E15A51293'. Variety Description Information For 'E15A51293' | |
|---|---|
| PHENOLOGY: | |
| Fruiting season length: | Medium |
| Relative maturity when grown in greenhouse: | Medium |
| FRUIT DISORDER RESISTANCE: | |
| Blotchy ripening: | Moderately susceptible |
| Catface: | Resistant |
| Fruit pox: | Resistant |
| Cracking, concentric: | Moderately resistant |
| Bursting: | Highly resistant |
| Blossom end rot: | Moderately resistant |
| Graywall: | Moderately resistant |
| Zippering: | Highly resistant |
| Gold fleck: | Moderately resistant |
| Cracking, radial: | Moderately resistant |
| Silvering: | Highly resistant |
| DISEASE AND PEST RESISTANCE: | |
| Tomato Spotted Wilt Virus (TSWV): | Resistant |
| Tomato Yellow Leaf Curl Virus (TYLCV): | Susceptible |
| Tobacco Mosaic Virus (ToMV) races 0, 1, and 2: | Resistant |
| Tomato Brown Rugose Fruit Virus (ToBRFV): | Highly resistant |
| *Clavibacter michiganensis* subsp. *michiganensis* (Cmm) (Bacterial canker): | Susceptible |
| *Pseudomonas corrugate* (Pc) (Pith necrosis): | Susceptible |
| *Pseudomonas syringae* pv. *tomato* (Pst) (Bacterial speck): | Susceptible |
| *Xanthomonas campestris* pv. *vesicatoria*, now *Xanthomonas* spp.) (Xcv, now X spp) (Bacterial spot): | Susceptible |
| *Ralstonia solanacearum* (Rs) (Bacterial wilt): | Susceptible |
| *Alternaria alternata* f. sp. *lycopersici* (Aal) (*Alternaria* stem canker): | Susceptible |
| *Fusarium oxysporum* f. sp. *radicis-lycopersici* (Forl) (*Fusarium* crown and root rot): | Susceptible |
| *Fusarium oxysporum* f. sp. *lycopersici* (Fol) (races 0, 1, and 2): | Highly resistant |
| *Verticillium albo-atrum* (Va) (race 0) and *Verticillium dahliae* (Vd) (race 0) (*Verticillium* wilt): | Resistant |
| *Alternaria solani* (As) (Early blight): | Susceptible |
| *Stemphylium solani* (Ss) (Grey leaf spot): | Susceptible |
| *Leveillula taurica*, anamorph: *Oidiopsis sicula* (Lt) (Powdery mildew): | Susceptible |
| *Pseudoidium neolycopersici* (ex *Oidium lycopersicum* (On)) (Pn) (Powdery mildew): | Susceptible |
| *Pyrenochaeta lycopersici*, now *Pseudopyrenochaeta lycopersici* (Pl) (Corky root rot): | Susceptible |
| *Meloidogyne arenaria* (Ma), *Meloidogyne incognita* (Mi), and *Meloidogyne javanica* (Mj) (root-knot nematodes): | Moderately resistant |
| Tomato fruitworm: | Susceptible |
| Spider mites: | Susceptible |
| Tobacco flea beetle: | Susceptible |
| Tomato hornworm: | Susceptible |
| Whitefly: | Susceptible |

Comparison of Hybrid Tomato 'E15A51293' to Other Tomato Varieties

Figure 3:
FIG. 3 shows a comparison between whole plants and fruit of commercial tomato variety '*paipai*' (unpatented; right) and hybrid tomato 'E15A51293' (left).

Hybrid tomato 'E15A51293' is similar to commercial tomato variety '*paipai* (unpatented). Column 1 of Table 2 shows the plant characteristics being compared, column 2 shows the characteristics of hybrid tomato 'E15A51293', and column 3 shows the characteristics of tomato '*paipai*'. Hybrid tomato 'E15A51293' is depicted in FIGS. 1A-1G, and a comparison to commercial tomato variety '*paipai*' is depicted in FIG. 3.

TABLE 2

Comparison of hybrid tomato 'E15A51293' to 'Paipai'.

| Characteristic | 'E15A51293' | 'Paipai' |
|---|---|---|
| Tomato Brown Rugose Fruit Virus (ToBRFV) | Highly resistant | Susceptible |
| *Fusarium oxysporum* f. sp. *lycopersici* (Fol) (races 0, 1, and 2) | Highly resistant | Susceptible |

Overview of Hybrid Tomato 'E15A51296'

Figure 2B:
FIGS. 2A-2H show hybrid tomato 'E15A51296'.
Figure 2A:
Figure 2D:
Figure 2C:
Figure 2F:
Figure 2E:
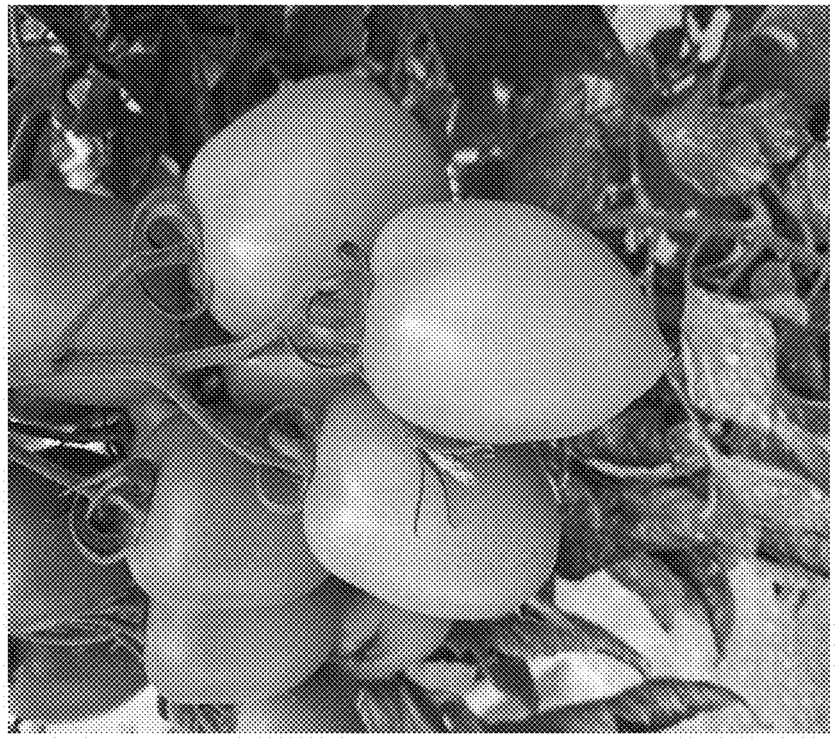
Figure 2H:
Figure 2G:

Hybrid tomato 'E15A51296' has medium to close leaf cover, produces 7 fruits per cluster and 15 clusters in production. 'E15A51296' is suitable for fresh market use. Further, hybrid tomato 'E15A51296' is adapted to greenhouse growing methods, in particular, to a hydroponic growing system. In addition, hybrid tomato 'E15A51296' is highly resistant to the pathogens Tomato Brown Rugose Fruit Virus (ToBRFV), resistant to the pathogens Tobacco Mosaic Virus (ToMV) races 0, 1, and 2, Tomato spotted wilt virus (TSWV), Tomato yellow leaf curl virus (TYLCV), *Fusarium oxysporum* f. sp. *lycopersici* (Fol) races 0, 1, and 2, and *Verticillium* wilt (*Verticillium albo-atrum* (Va), *Verticillium dahliae* (Vd) (races 0)); highly resistant to the fruit disorders bursting, zippering and silvering; resistant to the fruit disorders catface, fruit pox, graywall; and moderately resistant to the fruit disorders blotchy ripening, concentric cracking, blossom end rot, gold fleck and radial cracking. In addition, hybrid tomato 'E15A51296' is moderately resistant to the pests root-knot nematode (*Meloidogyne arenaria* (Ma), *Meloidogyne incognita* (Mi), *Meloidogyne javanica* (Mj)). FIG. 2A shows whole plants and fruit of hybrid tomato 'E15A51296'. FIG. 2B shows the upper sides of typical leaves of hybrid tomato 'E15A51296'. FIG. 2C shows the lower sides of typical leaves of hybrid tomato 'E15A51296'. FIG. 2D shows flowers of hybrid tomato 'E15A51296'. FIG. 2E shows green-mature fruit (center) of hybrid tomato 'E15A51296'. FIG. 2F shows the full ripe fruit (top) of hybrid tomato 'E15A51296'. FIG. 2G shows cross-sections (left) and longitudinal sections (right) of full-ripe tomato fruit of hybrid tomato 'E15A51296'. FIG. 2H shows 2-15 cm seedlings of hybrid tomato 'E15A51296' grown under optimal conditions. Hybrid tomato 'E15A51296' is the result of numerous generations of plant selections from its parent lines, and and was chosen for its plant size, strong vigor, medium to close leaf cover, good fruit setting, amount of fruit per cluster and number of fruit clusters produced, fruit weight, fruit shape and uniformity, and its resistances to Tobacco mosaic virus (ToMV) (resistant), Tomato Brown Rugose Fruit Virus (ToBRFV) (highly resistant), Tomato yellow leaf curl virus (TYLCV) (resistant), Tomato spotted wilt virus (TSWV) (resistant), *Verticillium* wilt, *Fusarium oxysporum* f. sp. *lycopersici* (Fol) (resistant), and root-knot nematode (moderately resistant). The resistance of this plant to ToBRV was of particular importance in selection.

Hybrid tomato 'E15A51296' has shown uniformity and stability for the traits, within the limits of environmental influence for the traits. The hybrid has been increased with continued observation for uniformity. No variant traits have been observed or are expected in hybrid tomato 'E15A51296'.

Objective Description of the Hybrid Tomato 'E15A51296'

In various embodiments, 'E15A51296' can be characterized by the following morphologic and other characteristics as outlined in Table 3. The data which define these characteristics is based on observations taken in Almería, Spain. Measurements of 'E15A51296' plants were made twenty weeks after seeding.

TABLE 3

| Morphologic and other characteristics of 'E15A51296'. Variety Description Information For 'E15A51296' | |
|---|---|
| SEEDLING: | |
| Anthocyanin in hypocotyl of 2-15 cm seedling: | Absent |
| Habit of 3-4 week old seedling: | Compact |
| MATURE PLANT: | |
| Plant height (in cm): | 600 to 700 |
| Growth type: | Indeterminate |
| Form: | Normal |
| Size of canopy: | Medium |
| Diameter (in cm): | 30 to 45 |
| Height (in cm): | 8 to 10 |
| Habit: | Erect |
| GROWTH CONDITION: | |
| Type of culture: | Greenhouse |
| Main use: | Fresh market |
| Mechanical harvest: | Not suitable |
| Suitable growing region(s): | Mexico, Spain |
| Planting period in adapted growth area: | Late August to late November |
| Harvesting period in adapted growth area: | November to June |
| Growing system: | Hydroponic |
| STEM: | |
| Branching: | Intermediate |
| Branching at cotyledonary or first node: | Absent |
| Number of nodes between first inflorescence: | 1 to 4 |
| Number of nodes between early (first to second, second to third) inflorescences: | 2 to 3 |
| Number of nodes between later developing inflorescences: | 2 to 3 |
| Pubescence on younger stems: | Moderately hairy |
| LEAF: | |
| Type of blade: | Tomato |
| Morphology: | Type 2 |
| Margin of major leaflets: | Nearly entire |
| Margin rolling or wiltiness: | Moderate |
| Onset of leaf rolling: | Late season |
| Surface of major leaflets: | Smooth |
| Pubescence: | Normal |

TABLE 3-continued

| Morphologic and other characteristics of 'E15A51296'. Variety Description Information For 'E15A51296' | |
|---|---|
| INFLORESCENCE: | |
| Type: | Simple |
| Average number of flowers in inflorescence: | 7 to 8 |
| Leafy or "running" inflorescences: | Absent |
| FLOWER: | |
| Calyx shape: | Normal, lobes awl-shaped |
| Calyx lobe length: | Approximately equaling corolla |
| Corolla color: | Yellow |
| Style pubescence: | Absent |
| Anthers: | Separating into two or more groups at anthesis |
| Fasciation (first flower of third inflorescence): | Absent |
| FRUIT: | |
| Typical fruit shape: | Obovate |
| Shape of transverse section: | Round |
| Shape of stem end: | Flat |
| Shape of blossom end: | Tapered |
| Shape of pistil scar: | Dot |
| Ribbing at peduncle end: | Absent or very weak |
| Abscission layer: | Present (pedicellate) |
| Point of detachment of fruit at harvest: | At pedicel joint |
| Pedicel length (from joint to calyx attachment, in mm): | 11 |
| Length of mature fruit (stem axis, in mm): | 120 |
| Diameter of fruit at widest point (in mm): | 65 |
| Average weight of mature fruit (in grams): | 160 to 162 |
| Number of locules: | 2-4 |
| Fruit surface: | Smooth |
| Green shoulder (before maturity): | Absent |
| Full ripe fruit color: | Red |
| Full ripe fruit flesh color: | Red/Crimson |
| Uniformity of flesh color: | Uniform |
| Stem scar size: | Small |
| Core: | Present |
| Thickness of pericarp (in mm): | 5 |
| Firmness: | Firm |
| Fruit shelf-life: | Long |
| PHENOLOGY: | |
| Fruiting season length: | Medium |
| Relative maturity when grown in greenhouse: | Medium |
| FRUIT DISORDER RESISTANCE: | |
| Blotchy ripening: | Moderately resistant |
| Catface: | Resistant |
| Fruit pox: | Resistant |
| Cracking, concentric: | Moderately resistant |
| Bursting: | Highly resistant |
| Blossom end rot: | Moderately resistant |
| Graywall: | Resistant |
| Zippering: | Highly resistant |
| Gold fleck: | Moderately resistant |
| Cracking, radial: | Moderately resistant |
| Silvering: | Highly resistant |
| DISEASE AND PEST RESISTANCE: | |
| Tomato Spotted Wilt Virus (TSWV): | Resistant |
| Tomato Yellow Leaf Curl Virus (TYLCV): | Resistant |
| Tobacco Mosaic Virus (ToMV) races 0-2: | Resistant |
| Tomato Brown Rugose Fruit Virus (ToBRFV): | Highly resistant |
| *Clavibacter michiganensis* subsp. *michiganensis* (Cmm) (Bacterial canker): | Susceptible |
| *Pseudomonas corrugate* (Pc) (Pith necrosis): | Susceptible |
| *Pseudomonas syringae* pv. *tomato* (Pst) (Bacterial speck): | Susceptible |
| *Xanthomonas campestris* pv. *vesicatoria*, now *Xanthomonas* spp.) (Xcv, now X spp) (Bacterial spot): | Susceptible |
| *Ralstonia solanacearum* (Rs) (Bacterial wilt): | Susceptible |
| *Alternaria alternata* f. sp. *lycopersici* (Aal) (*Alternaria* stem canker): | Susceptible |
| *Fusarium oxysporum* f. sp. *radicis-lycopersici* (Forl) (*Fusarium* crown and root rot): | Susceptible |

TABLE 3-continued

| Morphologic and other characteristics of 'E15A51296'. Variety Description Information For 'E15A51296' | |
|---|---|
| *Fusarium oxysporum* f. sp. *lycopersici* (Fol) (races 0, 1, and 2) (*Fusarium* wilt): | Resistant |
| *Verticillium albo-atrum* (Va) and *Verticillium dahliae* (Vd) (race 0) (*Verticillium* wilt): | Resistant |
| *Alternaria solani* (As) (Early blight): | Susceptible |
| *Stemphylium solani* (Ss) (Grey leaf spot): | Susceptible |
| *Leveillula taurica*, anamorph: *Oidiopsis sicula* (Lt) (Powdery mildew): | Susceptible |
| *Pseudoidium neolycopersici* (ex *Oidium lycopersicum* (On)) (Pn) (Powdery mildew): | Susceptible |
| *Pyrenochaeta lycopersici*, now *Pseudopyrenochaeta lycopersici* (Pl) (Corky root rot): | Susceptible |
| *Meloidogyne arenaria* (Ma), *Meloidogyne incognita* (Mi), and *Meloidogyne javanica* (Mj) (root-knot nematodes): | Moderately resistant |
| Tomato fruitworm: | Susceptible |
| Spider mites: | Susceptible |
| Tobacco flea beetle: | Susceptible |
| Tomato hornworm: | Susceptible |
| Whitefly: | Susceptible |

Comparison of Hybrid Tomato 'E15A51296' to Other Tomato Varieties

Figure 4:
FIG. 4 shows a comparison between whole plants and fruit of tomato '*quiroga*' (unpatented; left) and hybrid tomato 'E15A51296' (right).

Hybrid tomato 'E15A51296' is similar to commercial tomato variety '*quiroga*' (unpatented). Column 1 of Table 4 shows the plant characteristics being compared, column 2 shows the characteristics of hybrid tomato 'E15A51296', and column 3 shows the characteristics of tomato '*quiroga*'. Hybrid tomato 'E15A51296' is depicted in FIGS. 2A-2H, and the comparison to commercial tomato variety '*quiroga*' is depicted in FIG. 4.

TABLE 4

Comparison of hybrid tomato 'E15A51296' to 'Paipai'.

| Characteristic | 'E15A51296' | 'Quiroga' |
|---|---|---|
| Tomato Brown Rugose Fruit Virus (ToBRFV) | Highly resistant | Susceptible |

Further Embodiments

The present disclosure is further directed to methods for producing a tomato plant by crossing a first parent tomato plant with a second parent tomato plant where either the first or second parent tomato plant is hybrid tomato 'E15A51293' or 'E15A51296'. Further, both first and second parent tomato plants can come from hybrid tomato 'E15A51293' or 'E15A51296'. All plants produced using hybrid tomato 'E15A51293' or 'E15A51296' as a parent are within the scope of the disclosure, including plants derived from hybrid tomato 'E15A51293' or 'E15A51296'. Plants derived from hybrid tomato 'E15A51293' or 'E15A51296' may be used, in certain embodiments, for the development of new tomato varieties. By selecting plants having one or more desirable traits, a plant derived from hybrid tomato 'E15A51293' or 'E15A51296' is obtained which possesses some of the desirable traits of the hybrid as well as potentially other selected traits.

Further, any methods using hybrid tomato 'E15A51293' or 'E15A51296' are included in this disclosure: selfing, backcrosses, hybrid production, crosses to populations, and the like. Plants produced using hybrid tomato 'E15A51293' or 'E15A51296' as a parent are presented herein, including plants derived from 'E15A51293' or 'E15A51296'.

The development of new varieties using one or more starting varieties is well known in the art. In accordance with this disclosure, novel varieties may be created by crossing hybrid tomato 'E15A51293' or 'E15A51296' followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

It is preferred to breed for a combination of desirable plant characteristics and resistances to create a single variety or hybrid containing an improved combination of desirable traits from the parental germplasm. The development of commercial tomato hybrids relates to the development of tomato parental lines, the crossing of these lines, and the evaluation of the crosses. Hybrid varieties offer multiple advantages, including a combination of desirable dominant and recessive traits from a set of inbred parents. Pedigree breeding and recurrent selection breeding methods are used to develop cultivars from breeding populations. Breeding programs combine desirable traits from two or more varieties or various broad-based sources into breeding pools from which lines are developed by selfing and selection of desired phenotypes. The new lines are crossed with other lines and the hybrids from these crosses are evaluated to determine which have the desirable characteristics.

As used herein, the term "plant" includes plant cells, plant protoplasts, plant cell tissue cultures from which tomato plants can be regenerated, plant calli, plant clumps and plant cells that are intact in plants or parts of plants, such as embryos, pollen, ovules, flowers, leaves, stems, and the like.

Gene Conversions

When the terms "tomato plant", "hybrid", "cultivar", or "tomato line" are used in the context of the present disclosure, this also includes any single gene conversions of that variety. The term single gene converted plant as used herein refers to those tomato plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present disclosure to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental tomato plant that contributes the gene for the desired characteristic is termed the nonrecurrent or donor parent. This terminology refers to the fact that the nonrecurrent parent is used one time in the backcross protocol and therefore does not recur. The parental tomato plant to which the gene or genes from the nonrecurrent parent are transferred is known as the recurrent parent as it is used for several rounds in the backcrossing protocol (Poehlman & Sleper, 1994; Fehr, Principles of Cultivar Development pp. 261-286 (1987)). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a tomato plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add an agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Examples of single gene traits include, for example, male sterility, herbicide resistance, resistance for bacterial, fungal, or viral disease, insect resistance, male fertility, enhanced nutritional quality, industrial usage, yield stability, yield enhancement, modified fatty acid metabolism, modified carbohydrate metabolism, and/or nematode resistance. These genes are generally inherited through the nucleus. Several of these single gene traits are described in U.S. Pat. Nos. 5,959,185; 5,973,234, 5,777,196, 5,948,957, 5,969,212, and 5,977,445.

Tissue Culture

Further reproduction of a tomato variety can occur by tissue culture and regeneration. Tissue culture of various tissues of tomatoes and regeneration of plants therefrom is well known and widely published. For example, reference may be had to Girish-Chandel et al., Advances in Plant Sciences, 2000, 13: 1, 11-17; Costa et al., Plant Cell Report, 2000, 19:3 327-332; Plastira et al., Acta Horticulturae, 1997, 447, 231-234; Zagorska et al., Plant Cell Report, 1998, 17: 12 968-973; Asahura et al., Breeding Science, 1995, 45: 455-459; Chen et al., Breeding Science, 1994, 44: 3, 257-262, Patil et al., Plant and Tissue and Organ Culture, 1994, 36: 2, 255-258; Gill, R., et al., Somatic Embryogenesis and Plant Regeneration from Seedling Cultures of Tomato (*Lycopersicon esculentum* Mill.), J. Plant Physiol., 147:273-276 (1995); Jose M. Segui-Simarro and Fernando Nuez, Embryogenesis induction, callogenesis, and plant regeneration by in vitro culture of tomato isolated microspores and whole anthers J. Exp. Bot., March 2007; 58: 1119-1132; Hamza et al., Re-evaluation of Conditions for Plant Regeneration and *Agrobacterium*-Mediated Transformation from Tomato (*Lycopersicon esculentum*), J. Exp. Bot., December 1993; 44: 1837-1845. It is clear from the literature that the state of the art is such that these methods of obtaining plants are routinely used and have a very high rate of success. Thus, another aspect of this disclosure is to provide cells which upon growth and differentiation produce tomato plants having the physiological and morphological characteristics of hybrid tomato 'E15A51293' or 'E15A51296'.

As used herein, the term "tissue culture" indicates a composition containing isolated cells of the same or a different type or a collection of such cells organized into parts of a plant. Exemplary types of tissue cultures are protoplasts, calli, plant clumps, meristematic cells, and plant cells that can generate tissue culture that are intact in plants or parts of plants, such as embryos, pollen, flowers, seeds, fruit, petioles, leaves, stems, roots, root tips, anthers, pistils and the like. Means for preparing and maintaining plant tissue culture are well known in the art. By way of example, a tissue culture containing organs has been used to produce regenerated plants. U.S. Pat. Nos. 5,959,185; 5,973,234 and 5,977,445 describe certain techniques.

Vegetative Propagation

Tomato plants can also be propagated vegetatively. Accordingly, the present disclosure is further directed to vegetative propagation of hybrid tomato 'E15A51293' or 'E15A51296'. A part of the plant, for example a shoot tissue, is collected and a new plant is obtained from the part. Such part typically includes an apical meristem of the plant. The collected part is transferred to a medium allowing development of a plantlet including, for example, rooting or development of shoots, or is grafted onto a tomato plant or a rootstock prepared to support growth of shoot tissue. This is achieved using methods well-known in the art. Accordingly, in one embodiment, a method of vegetatively propagating a tomato plant of the present disclosure involves collecting a part of a plant according to the present disclosure, e.g., a shoot tissue, and obtaining a plantlet from said part. In one embodiment, a method of vegetatively propagating a tomato plant of the present disclosure involves: (a) collecting tissue of a plant of the present disclosure; and (b) rooting said proliferated shoots to obtain rooted plantlets. In one embodiment, a method of vegetatively propagating a plant of the present disclosure involves: (a) collecting tissue of a plant of the present disclosure; (b) cultivating said tissue to obtain proliferated shoots; and (c) rooting said proliferated shoots to obtain rooted plantlets. In one embodiment, such methods further involve growing a plant from said plantlets. In one embodiment, a fruit is harvested from said plant.

Additional Breeding Methods

Tomato varieties such as hybrid tomatoes 'E15A51293' or 'E15A51296' are typically developed for use as fresh produce or for processing. However, tomato varieties also provide a source of breeding material that may be used to develop new tomato varieties. Plant breeding techniques known in the art and used in a tomato plant breeding program may include, for example, chasing selfs, recurrent selection, mass selection, bulk selection, mutation breeding, backcrossing, pedigree breeding, open pollination breeding, restriction fragment length polymorphism enhanced selection, genetic marker enhanced selection, making double haploids, and transformation. Often combinations of these techniques are used. The development of tomato varieties in a plant breeding program involves, in general, the development and evaluation of homozygous varieties. There are many analytical methods available to evaluate a new variety. The oldest and most traditional method of analysis is the observation of phenotypic traits, but genotypic analysis may also be used. Thus, another aspect of the disclosure is to provide hybrid tomato 'E15A51293' or 'E15A51296' as a source of breeding material for the development of new tomato varieties using, for example, the breeding techniques described herein. One of skill in the art would recognize that additional breeding techniques may exist and may be used to develop new tomato varieties using hybrid tomato 'E15A51293' or 'E15A51296'.

The present disclosure is directed to methods for producing a tomato plant by crossing a first parent tomato plant with a second parent tomato plant where either the first or second parent tomato plant is hybrid tomato 'E15A51293' or 'E15A51296'. The other parent may be any other tomato plant, such as a tomato plant that is part of a synthetic or natural population. Further, both first and second parent tomato plants can come from tomato hybrid 'E15A51293' or 'E15A51296'. Any such methods using hybrid tomato 'E15A51293' or 'E15A51296' are part of this disclosure: selfing, sibbing, backcrosses, mass selection, pedigree breeding, bulk selection, hybrid production, crosses to populations, and the like. These methods are well known in the art and some of the more commonly used breeding methods are described herein. Descriptions of breeding methods can be found in one of several reference books (e.g., Allard, Principles of Plant Breeding, 1960; Simmonds, Principles of Crop Improvement, 1979; Sneep et al., 1979; Fehr, "Breeding Methods for Cultivar Development," 2.sup.nd ed., Wilcox editor, 1987).

All plants produced using tomato hybrid 'E15A51293' or 'E15A51296' as at least one parent are within the scope of this disclosure, including those developed from cultivars derived from tomato hybrid 'E15A51293' or 'E15A51296'.

Advantageously, the tomato cultivars of the present disclosure can be used in crosses with other, different, tomato plants to produce the first generation ($F_1$) tomato hybrid seeds and plants with superior characteristics. The cultivars of the disclosure can also be used for transformation where exogenous genes are introduced and expressed by the cultivars of the disclosure. Genetic variants created either through traditional breeding methods using tomato hybrid 'E15A51293' or 'E15A51296', or through transformation of hybrid tomato 'E15A51293' or 'E15A51296' by any of a number of protocols known to those of skill in the art, are within the scope of this disclosure.

The following describes exemplary breeding methods that may be used with hybrid tomato 'E15A51293' or 'E15A51296' in the development of further tomato plants. One such embodiment is a method for developing an 'E15A51293' or 'E15A51296' progeny tomato plant in a tomato plant breeding program involving: obtaining the tomato plant, or a part thereof, of 'E15A51293' or 'E15A51296', utilizing said plant or plant part as a source of breeding material, and selecting an 'E15A51293' or 'E15A51296' progeny plant with molecular markers in common with 'E15A51293' or 'E15A51296' and/or with morphological and/or physiological characteristics selected from the characteristics listed in any one of Tables 1-6. Breeding steps that may be used in the tomato plant breeding programs may include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of 'E15A51293' or 'E15A51296' progeny tomato plants, involving crossing hybrid tomato 'E15A51293' or 'E15A51296' with another tomato plant, thereby producing a population of tomato plants, which, on average, derive 50% of their alleles from 'E15A51293' or 'E15A51296'. A plant of this population may be selected and repeatedly selfed or sibbed with a tomato cultivar resulting from these successive filial generations. In one embodiment, the tomato cultivar produced by this method has obtained at least 50% of its alleles from 'E15A51293' or 'E15A51296'.

Additional methods include, without limitation, chasing selfs. Chasing selfs involves identifying inbred plants among tomato plants that have been grown from hybrid tomato seed. Once the seed is planted, the inbred plants may be identified and selected due to their decreased vigor relative to the hybrid plants that grow from the hybrid seed. By locating the inbred plants, isolating them from the rest of the plants, and self-pollinating them (i.e., "chasing selfs"), a breeder can obtain an inbred line that is identical to an inbred parent used to produce the hybrid.

Accordingly, another aspect of the present disclosure relates a method for producing an inbred tomato variety by: planting seed of the tomato variety 'E15A51293' or 'E15A51296'; growing plants from the seed; identifying one or more inbred tomato plants; controlling pollination in a manner which preserves homozygosity of the one or more inbred plants; and harvesting resultant seed from the one or more inbred plants. The step of identifying the one or more inbred tomato plants may further include identifying plants with decreased vigor, i.e., plants that appear less robust than plants of the tomato variety 'E15A51293' or 'E15A51296'. Tomato plants capable of expressing substantially all of the physiological and morphological characteristics of the parental inbred lines of tomato variety 'E15A51293' or 'E15A51296' include tomato plants obtained by chasing selfs from seed of tomato variety 'E15A51293' or 'E15A51296'.

One of ordinary skill in the art will recognize that once a breeder has obtained inbred tomato plants by chasing selfs from seed of tomato variety 'E15A51293' or 'E15A51296', the breeder can then produce new inbred plants such as by sib-pollinating, or by crossing one of the identified inbred tomato plant with a plant of the tomato variety 'E15A51293' or 'E15A51296'.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus, the disclosure includes 'E15A51293' or 'E15A51296' progeny tomato plants containing a combination of at least two traits of hybrid tomato 'E15A51293' or 'E15A51296', the traits being selected from those listed in Table 1, Table 3, or Table 5, so that the progeny tomato plant is not significantly different for the traits than 'E15A51293' or 'E15A51296' as determined at the 5% significance level when grown in the same environmental conditions. Using techniques described herein, molecular markers may be used to identify said progeny plant as an 'E15A51293' or 'E15A51296' progeny plant. For each of the evaluation schemes involving hybrid tomato 'E15A51293' or 'E15A51296', mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of 'E15A51293' or 'E15A51296' may also be characterized through their filial relationship with 'E15A51293' or 'E15A51296', as for example being within a certain number of breeding crosses of 'E15A51293' or 'E15A51296'. A breeding cross is a cross made to introduce new genetics into the progeny, and is distinguished from a cross, such as a self or a sib cross, made to select among existing genetic alleles. The lower the number of breeding crosses in the pedigree, the closer the relationship between 'E15A51293' or 'E15A51296', and its progeny. For example, progeny produced by the methods described herein may be within 1, 2, 3, 4 or 5 breeding crosses of 'E15A51293' or 'E15A51296'.

Exemplary breeding techniques are further described herein and may be used in breeding schemes using hybrid tomato 'E15A51293' or 'E15A51296'.

Backcross Conversion

Hybrid tomatoes 'E15A51293' or 'E15A51296' represent new base genetic varieties into which a new locus or trait may be introgressed. Backcrossing represents an important method that can be used to accomplish such an introgression. The terms backcross conversion and single locus conversion are used interchangeably to designate the product of a backcrossing program.

A backcross conversion of a tomato variety such as, for example, hybrid tomato 'E15A51293' or 'E15A51296', occurs when DNA sequences are introduced through backcrossing (Hallauer et al, 1988, "Corn Breeding" Corn and Corn Improvements, No. 18, pp. 463-481), with the tomato variety utilized as the recurrent parent. A backcross conversion may produce a plant with one or more desired genes or traits (e.g., 1, 2, 3, 4, or 5 and/or no more than 6, 5, 4, 3, or 2) in at least two or more backcrosses (e.g., at least 2, 3, 4, 5 or more crosses). Poehlman, Breeding Field Crops, P. 204 (1987) suggests from one to four or more backcrosses, but the number of backcrosses necessary can be reduced with the use of molecular markers. In addition, an herbicide resistance gene may be used as a selectable marker and/or as a phenotypic trait.

Other factors, such as a genetically similar donor parent, may also reduce the number of backcrosses necessary. As noted by Poehlman, 1987, backcrossing is easiest for simply inherited, dominant and easily recognized traits, but may be done with recessive alleles as well. The last backcross generation is usually selfed to give pure breeding progeny for the gene(s) being transferred, although a backcross conversion with a stably introgressed trait may also be maintained by further backcrossing to the recurrent parent with selection for the converted trait.

A single locus conversion of site specific integration system allows for the integration of multiple genes at the converted loci. Along with selection for the trait of interest, progeny are selected for the phenotype of the recurrent parent. The backcross is a form of inbreeding, and the features of the recurrent parent are automatically recovered after successive backcrosses (Poehlman, 1987).

While a number of exemplary methods are described above, any methods or combinations of methods for producing hybrid tomato 'E15A51293' or 'E15A51296', and any methods or combinations of methods using hybrid tomato 'E15A51293' or 'E15A51296' are included in the present disclosure. Descriptions of other breeding methods that are commonly used for different traits and crops can be found in one of several reference books (e.g., Allard, 1960; Simmonds, 1979; Sneep et al., 1979; Fehr, 1987). Additional non-limiting examples of methods that are known in the art of using and/or producing hybrid tomato 'E15A51293' or 'E15A51296' include pedigree breeding, recurrent selection, mass selection, bulk selection, mutation breeding, open pollination breeding, restriction fragment length polymorphism enhanced selection, genetic marker enhanced selection, breeding with molecular markers, transformation, and production of double haploids.

The use of the terms "a," "an," and "the," and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments of the disclosure and does not pose a limitation on the scope of the disclosure unless otherwise claimed. No language in the specification should be construed as indicating any non-claimed element as essential to the practice of the embodiments of the disclosure.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

Hybrid Tomato 'E15A51293'

A deposit of at least 625 seeds of the tomato variety 'E15A51293' was made with the National Collection of Industrial, Food and Marine Bacteria Ltd. (NCIMB Ltd), Wellheads Place, Dyce, Aberdeen, AB21 7 GB, United Kingdom, and assigned NCIMB Number X1. The seeds deposited with the NCIMB on DATE were obtained from the seed of the variety maintained by Enza Zaden USA, 7 Harris Place, Salinas, California 93901, United States, since prior to the filing date of the application. Access to this deposit will be available during the pendency of this application to persons determined by the Commissioner of Patents and Trademarks to be entitled thereto under 37 C.F.R. § 1.14 and 35 U.S.C. § 122. Upon issuance, the Applicant will make the deposit available to the public consistent with all of the requirements of 37 C.F.R. § 1.801-1.809. This deposit of the tomato variety 'E15A51293' will be maintained in the NCIMB, which is a public depository, for a period of 30 years, or at least 5 years after the most recent request for a sample of the deposit, or for the effective life of the patent, whichever is longer, and will be replaced if it becomes nonviable during that period. Applicant has no authority to waive any restrictions imposed by law on the transfer of biological material or its transportation in commerce. Applicant does not waive any infringement of rights granted under this patent or under the Plant Variety Protection Act (7 USC 2321 et seq.).

Hybrid Tomato 'E15A51296'

A deposit of at least 625 seeds of the tomato variety 'E15A51296' was made with the National Collection of Industrial, Food and Marine Bacteria Ltd. (NCIMB Ltd), Wellheads Place, Dyce, Aberdeen, AB21 7 GB, United Kingdom, and assigned NCIMB Number 44230. The seeds deposited with the NCIMB on Sep. 13, 2023 were obtained from the seed of the variety maintained by Enza Zaden USA, 7 Harris Place, Salinas, California 93901, United States, since prior to the filing date of the application. Access to this deposit will be available during the pendency of this application to persons determined by the Commissioner of Patents and Trademarks to be entitled thereto under 37 C.F.R. § 1.14 and 35 U.S.C. § 122. Upon issuance, the Applicant will make the deposit available to the public consistent with all of the requirements of 37 C.F.R. § 1.801-1.809. The viability of this deposit of the seeds of hybrid tomato variety 'E15A51296' was tested and confirmed at the time of deposit. This deposit of the tomato variety 'E15A51296' will be maintained in the NCIMB, which is a public depository, for a period of 30 years, or at least 5 years after the most recent request for a sample of the deposit, or for the effective life of the patent, whichever is longer, and will be replaced if it becomes nonviable during that period. Applicant has no authority to waive any restrictions imposed by law on the transfer of biological material or its transportation in commerce. Applicant does not waive any infringement of rights granted under this patent or under the Plant Variety Protection Act (7 USC 2321 et seq.).

Breeding History of Hybrid Tomato 'E15A51296'

The hybrid tomato variety 'E15A51296' (also known as 'Cedros', representative sample seed having been deposited under NCIMB Accession Number 44230) is a single cross hybrid of the homozygous female parental line OT5673 and the homozygous male parental line OT5506. Both parental breeding lines are proprietary breeding lines produced by the vegetable breeding company Enza Zaden and are not publicly available.

The invention claimed is:

1. A hybrid tomato seed designated as 'E15A51296', representative sample of seed having been deposited under NCIMB Accession Number 44230.

2. A tomato plant produced by growing the seed of claim 1.

3. A plant part from the plant of claim 2.

4. The plant part of claim 3, wherein said part is a leaf, an ovule, a pollen grain, a fruit, or a cell.

5. The plant part of claim 4, wherein said part is a fruit.

6. A tomato plant having all the physiological and morphological characteristics of the tomato plant of claim 2.

7. A plant part from the plant of claim 6, wherein said part is a leaf, an ovule, a pollen grain, a fruit, or a cell.

8. The plant part of claim 7, wherein said part is a fruit.

9. A pollen grain or an ovule of the plant of claim 2.

10. A protoplast produced from the plant of claim 2.

11. A tissue or cell culture produced from cells or protoplasts from the plant of claim 2, wherein said cells or protoplasts are produced from a plant part selected from the group consisting of root, root tip, meristematic cell, stem, hypocotyl, petiole, cotyledon, leaf, flower, anther, pollen, pistil, and fruit.

12. A tomato plant regenerated from the tissue culture of claim 11, wherein the plant has all of the morphological and physiological characteristics of a tomato plant produced by growing seed designated as 'E15A51296', representative sample of seed having been deposited under NCIMB Accession Number 44230.

13. A method of making tomato seeds, said method comprising crossing the plant of claim 2 with another tomato plant and harvesting seed therefrom.

14. A method of producing a seed derived from the 'E15A51296' tomato plant of claim 2, comprising the steps:

a) crossing a hybrid tomato designated as 'E15A51296', representative sample of seed having been deposited under NCIMB Accession Number 44230, with itself or a second tomato plant; and b) allowing seed of an 'E15A51296'-derived tomato plant to form.

15. The method of claim 14 further comprising:

c) crossing a plant grown from 'E15A51296'-derived tomato seed with itself or a second tomato plant to yield additional 'E15A51296'-derived tomato seed;

d) growing the additional 'E15A51296'-derived tomato seed of step (c) to yield additional 'E15A51296'-derived tomato plants; and e) repeating the crossing and growing of steps (c) and (d) for at least one additional generation to generate further 'E15A51296'-derived tomato plants.

16. The method of claim 15, wherein the crossing and growing steps (c) and (d) are repeated for an additional 3-10 generations.

17. A method of vegetatively propagating a plant of tomato variety designated as 'E15A51296', the method comprising the steps of:

a) collecting tissue capable of being propagated from a plant of hybrid tomato variety 'E15A51296', representative seed of said hybrid tomato variety having been deposited under NCIMB Accession Number 44230;

b) cultivating the tissue to obtain proliferated shoots; and c) rooting the proliferated shoots to obtain rooted plantlets.

18. The method of claim 17, further comprising step (d) growing plants from the rooted plantlets.

19. A method of producing a tomato fruit, said method comprising growing the plant of claim 2 until it sets at least one fruit, and harvesting the fruit.

* * * * *